United States Patent [19]

Gardner

[11] Patent Number: 4,532,123

[45] Date of Patent: Jul. 30, 1985

[54] DUAL MICROCAPSULES AND PROCESS FOR THEIR PREPARATION

[75] Inventor: David L. Gardner, Bellville, Ohio

[73] Assignee: Battelle Development Corporation, Columbus, Ohio

[21] Appl. No.: 466,500

[22] Filed: Feb. 18, 1983

Related U.S. Application Data

[63] Continuation-in-part of Ser. No. 402,164, Jul. 26, 1982, abandoned, which is a continuation-in-part of Ser. No. 354,869, Mar. 4, 1982, abandoned.

[51] Int. Cl.$^3$ .................. A61J 3/07; A61K 9/52; B01J 13/02

[52] U.S. Cl. .................. 424/21; 71/DIG. 1; 264/4.1; 264/4.3; 424/19; 424/20; 424/35; 424/94; 424/DIG. 7; 428/402.2; 428/402.21

[58] Field of Search .................. 264/4.1, 4.3; 428/402.2, 402.21; 424/19, 20, 35, 94, DIG. 7, 21; 210/643; 71/DIG. 1

[56] References Cited

U.S. PATENT DOCUMENTS

| | | | |
|---|---|---|---|
| 3,173,878 | 3/1961 | Reyes | 252/182 X |
| 3,242,051 | 3/1966 | Hiestand et al. | 264/4.3 X |
| 3,429,827 | 2/1969 | Ruus | 252/188.31 X |
| 3,493,652 | 2/1970 | Hartman | 424/35 X |
| 3,532,662 | 10/1970 | Ansdell | 523/206 X |
| 3,578,605 | 5/1971 | Baxter | 424/34 X |
| 3,725,113 | 4/1973 | Chang | 424/35 X |
| 3,773,919 | 11/1973 | Boswell et al. | 424/19 |
| 3,897,308 | 7/1975 | Li et al. | 435/177 |
| 3,922,338 | 11/1975 | Estevenel et al. | 424/21 |
| 3,962,414 | 6/1976 | Michaels | 424/19 |
| 4,016,099 | 4/1977 | Wellman et al. | 264/4.1 X |
| 4,076,774 | 2/1978 | Short | 264/4 |
| 4,111,201 | 9/1978 | Theeuwes | 424/19 X |
| 4,118,336 | 10/1978 | Morishita et al. | 424/35 X |
| 4,183,918 | 1/1980 | Asher et al. | 424/94 |
| 4,211,668 | 7/1980 | Tate | 264/4 X |
| 4,254,201 | 3/1981 | Sawai et al. | 430/111 |

OTHER PUBLICATIONS

Chang: "Semipermeable Aqueous Microcapsules as Artificial Cells", McGill *University Ph.D. Thesis*, Montreal, (Apr. 1965), pp. 93–96.

Chang: "Artificial Cells", C. C. Thomas–Publisher, (1972), pp. 15–19 and 36–42.

*Primary Examiner*—Richard D. Lovering
*Attorney, Agent, or Firm*—Biebel, French & Nauman

[57] ABSTRACT

Dual Microcapsules are disclosed. The outer membrane encapsulates a liquid having one or more smaller microcapsules (Mini-Microcapsules) suspended therein. The Mini-Microcapsules contain a conjugate or a reaction product of a Drug which diffuses into the liquid in which Mini-Microcapsules are suspended. The suspending liquid contains an enzyme which reacts with Drug complex or reaction product to regenerate or release the Drug. The drug diffuses through the outer membrane into a host.

22 Claims, 3 Drawing Figures

DUAL MICROCAPSULES AND PROCESS FOR THEIR PREPARATION

CROSS REFERENCE TO RELATED APPLICATIONS

This application is a continuation-in-part of the applicant's copending application Ser. No. 402,164, filed on July 26, 1982, now abandoned, which in turn is a continuation-in-part of the applicant's prior copending application Ser. No. 354,869, filed Mar. 4, 1982, abandoned.

BACKGROUND OF THE INVENTION

An increasingly important process for delivering a functional material to a particular locus involves the use of microcapsules. As the term is used in the art, a microcapsule is a functional material encapsulated in a membrane.

An important application of microcapsules is in the medical arts. In this field of application, a functional drug is encapsulated in a membrane that is semipermeable to the drug. When the drug is administered to the host, the drug is transported across the semipermeable membrane to release the drug to the host.

While the use of microcapsules for drug administration is widely employed, the method suffers from certain shortcomings which limits its further application in this art. Specifically, the rate at which the drug is released to the patient is controlled by the rate at which the drug is transported across the semipermeable membrane. While many types of polymeric materials providing different diffusion rates can be employed as the semipermeable membrane, each membrane has a limited range of permeability which effectively controls the rate at which a drug of interest is released to the host. For many purposes, the drug release rate may be too slow or too rapid to provide the desired drug release rate.

Accordingly, there is a need in the art for more refined and structurally modified microcapsules having the ability to release drugs to a host over a wide range of preselected rates.

SUMMARY OF THE INVENTION

The invention is directed to certain novel microcapsules which can be employed to release a wide variety of drugs to a host over a wide range of preselected drug release rates. The microcapsules of the invention are hereinafter characterized as dual microcapsules in that they include an outer semipermeable membrane which encapsulates two separate and distinct encapsulated components. One encapsulated component is a liquid material. The second encapsulated component is a smaller microcapsule, hereinafter referred to as a mini-microcapsule. The mini-microcapsule has a functional material encapsulated therein.

In a preferred embodiment of the invention, the two separately encapsulated components, one encapsulated by the outer membrane and the other encapsulated by the membrane of the mini-microcapsule, are reactive with each other. The component encapsulated within the mini-microcapsule diffuses across the wall of the mini-microcapsule to contact the component encapsulated within the outer membrane of the microcapsule. The two components then interact to generate a new entity not originally present per se in either of the two encapsulated components. The new entity then diffuses through the outer membrane and is released to the host.

In another embodiment of the invention, a single component is encapsulated in the mini-microcapsule with the second component encapsulated by the outer membrane serving solely or principally as a transport medium for the agent encapsulated within the mini-microcapsule. The two membranes included in the dual microcapsule will be fabricated from different polymeric materials and will have different diffusion rates for the component encapsulated within the mini-microcapsule.

The invention also is directed to methods for preparing the dual microcapsules of the invention.

The invention is further directed to methods for preparing certain mini-microcapsules employed in the manufacture of the dual microcapsules of the invention.

DEFINED TERMS

Figure 1:
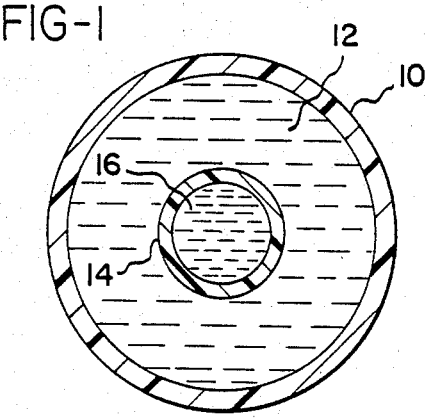
FIG. 1 is a sectional view of a dual microcapsule of the invention.

As an aid in interpreting the descriptions of the inventions which follow, the following terms will have the special meanings set forth below.

"Microcapsule" is an article of manufacture having a Functional Core Material encapsulated within a polymeric membrane. While Microcapsules may have essentially any physical form, they customarily are essentially spherical in shape and customarily have average diameters in the range of about 1 $\mu$m to 2,000 $\mu$m.

"Functional Core Material" is any solid or liquid material, other than a Mini-Microcapsule, encapsulated in a Microcapsule.

"Dual Microcapsule" is a special Microcapsule having at least two components encapsulated within the exterior membrane of the capsule. At least one of the two components will be a Microcapsule having a diameter smaller than the external membrane of the Dual Microcapsule, such small encapsulated microcapsules hereafter being identified as Mini-Microcapsules. A Dual Microcapsule may have two or more different types of Mini-Microcapsules encapsulated therein.

"Mini-Microcapsule" is a Microcapsule sufficiently small to be encapsulated within the interior of a Dual Microcapsule.

"Encapsulating Process" is any process for encapsulating a Functional Core Material in a polymeric membrane.

"Phase Separation Encapsulation Process" is a process for preparing Microcapsules in which the Functional Core Material to be encapsulated is dispersed, customarily by stirring, in a solvent solution of a polymer. While continuing stirring to keep the Functional Core Material uniformly dispersed throughout the polymer solution, a nonsolvent liquid is added to the polymer solution to change the polymer solubility in the medium and cause a phase separation of the dissolved polymer. Depending upon the specific polymer/solvent system, the polymer either precipitates from the solution or two immiscible liquid phases are produced, one of which is rich in polymer and polymer solvent and poor in nonsolvent, and the second of which is rich in nonsolvent and poor in solvent and polymer. Under certain conditions, the polymer rich phase will migrate to the interface between the dispersed droplets/particles and the continuous phase (non-solvent rich dispersing medium). The suspended particles of the Functional Core Material are encapsulated with the polymer and are subsequently hardened and recovered from the solvent/nonsolvent medium.

"Conjugate" is a product formed between two materials, one characterized as the "Functional Agent" and the second as the "Carrier", both of these terms being subsequent defined. The Conjugate is an entity separate and distinct from the Functional Agent and the Carrier. The Conjugate can be either a true chemical reaction product of the Functional Agent and the Carrrier or can be any type of complex formed therebetween. In either event, the Conjugate can be subsequently treated with another material characterized as a Deconjugating Agent (subsequently described) to reform at least a portion of the originally employed Functional Agent.

"Functional Agent" is an entity which performs a specific identifiable function.

"Carrier" is a material which will react with or form a complex with a Functional Agent.

"Drug" is a Functional Agent having a desirable beneficial physiological effect upon a host.

"Drug Conjugate" is a Conjugate in which the Functional Agent included therein is a Drug.

"Prodrug" is a term sometimes used interchangeably with Drug Conjugate, usually to define a Conjugate which is formed by effecting a chemical reaction between a Drug and a Carrier.

"Deconjugating Agent" is an agent capable of interacting with a Conjugate to liberate or reform at least a portion of the Functional Agent employed in the preparation of the Conjugate.

"CAB" is a cellulose acetate butyrate polymer. Such polymers are known in the art, are described in numerous patents and publications and are commercially available from multiple sources including Eastman Chemicals.

"PLA" is a polymer of lactic acid. Such polymers are known in the art. See U.S. Pat. No. 3,991,776.

"Dalton" is a term becoming increasingly popular in the art to designate molecular weight. A Dalton number is numerically equivalent to a gram molecular weight. By way of example, the Dalton number of sucrose is 342.

"Solvent" is an organic liquid having the power to dissolve at least 0.1 weight % of a designated polymer of interest at ambient temperature.

"Nonsolvent" is an organic liquid miscible with a solvent and having little or no solvent power for a designated polymer of interest at ambient temperature.

"Crenate Shape" is the shape assumed by an article having a flexible membrane supported by an internal fluid after the supporting fluid is evacuated from the membrane. The shape assumed by a deflated basketball bladder after the bulk of the air has diffused therefrom is a prime example of a Crenate Shape.

DETAILED DESCRIPTION OF THE INVENTION

FIG. 1 represents an embodiment of the invention containing a single Mini-Microcapsule encapsulated within another larger Microcapsule to form a Dual Microcapsule. The structure contains an outer polymeric membrane 10. A first liquid 12 is encapsulated within membrane 10. A Mini-Microcapsule having a polymeric membrane 14 is encapsulated within membrane 10. A second liquid 16 is encapsulated within membrane 14. In the most preferred embodiment of the invention, liquids 12 and 16 are aqueous liquids, with liquid 16 having a Conjugate dissolved or dispersed therein and liquid 12 having a Deconjugating Agent dissolved or dispersed therein. The membrane 14 will be semipermeable with respect to the Conjugate within liquid 16. Upon diffusing through membrane 14 and contacting the Deconjugating Agent within liquid 12, an interaction takes place to regenerate the Functional Agent. The Functional Agent then diffuses through membrane 10 into the system of the host. The structure shown in FIG. 1 is the structure of the Dual Microcapsule as it is prepared.

Figure 1A:
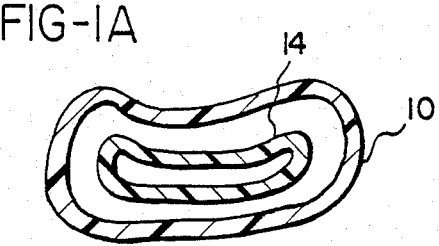
FIG. 1A is a sectional view of the dual microcapsule of FIG. 1 which has been dehydrated to remove the bulk of the water from the aqueous media originally present within the dual microcapsule, including the encapsulated mini-microcapsule.

In one of the preferred embodiments of the invention, the membranes 10 and 14 shown in FIG. 1 are semipermeable to water and can be dehydrated by processes subsequently described so as to remove the bulk of the water from both aqueous liquid 12 and aqueous liquid 16. The approximate Crenate Shape that the dehydrated Dual Microcapsule takes is shown in FIG. 1A. The bulk of the solids of original liquid 16 is maintained within membrane 14. The bulk of the solids originally present in liquid 12 is maintained in the space between membranes 10 and 14. When the dehydrated Dual Microcapsule of FIG. 1A is placed in contact with water, it imbides water so as to dissolve or disperse the solids encapsulated within membranes 10 and 14 to reform the Dual Microcapsule in substantially the form illustrated in FIG. 1.

In other embodiments of the invention, the liquid 16 may be a simple solution or dispersion of a Functional Agent in a suitable liquid, usually water, and liquid 12 will contain no material reactable with the Functional Agent and will serve principally as a transport medium for the Functional Agent. In such embodiments, membranes 10 and 14 will be fabricated from different polymeric materials so that the membranes will have different diffusion rates for the Functional Agent, with membrane 14 being significantly less permeable than membrane 10.

Figure 2:
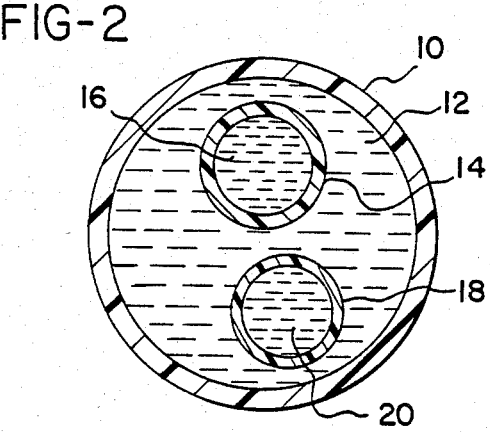
FIG. 2 is a sectional view of a dual microcapsule having two different mini-microcapsules encapsulated therein.

FIG. 2 illustrates another embodiment of the invention in which the Dual Microcapsule contains encapsulated therein two different Mini-Microcapsules. The second Mini-Microcapsule will include a polymeric membrane 18 encapsulating a third liquid 20. The membrane 18 and the liquid 20 customarily will differ in at least minor respects from the corresponding elements of the other Mini-Microcapsule.

The physical size of the Dual Microcapsules is not ordinarily a matter of critical importance in the practice of the invention. Customarily, the dual microcapsules will have outer diameters in the range of from about 20 μm to 2 mm. The physical size of the Mini-Microcapsules will be such that they easily fit within the outer membrane of the dual microcapsules. Typically, the Mini-Microcapsules will have diameters in the range of from about 1 μm to 1 mm.

The dual microcapsules can be prepared by a modification of the Phase Separation Encapsulation Process defined earlier herein. In this process, the liquid material to be encapsulated and the mini-microcapsules are suspended and stirred in the polymer solution to uniformly disperse the liquid material and the Mini-Microcapsules as a fine dispersion throughout the polymer solution. It is observed that the liquid material tends to cling to the outer membranes of the Mini-Microcapsules. While continuing stirring to keep the liquid material and the Mini-Microcapsules uniformly dispersed throughout the polymer solution, a nonsolvent liquid is added to the polymer solution to change the polymer solubility in the medium and cause a phase separation of the dissolved polymer. As earlier noted, the polymer either precipitates from the solution or two immiscible liquid phases are produced, one of which is rich in polymer and polymer solvent and poor in nonsolvent, and the second of which is rich in the nonsolvent and poor in solvent and polymer. By this means, the suspended particles of the liquid and the Mini-Microcapsules are encapsulated with the polymer which forms the outer membrane of the Dual Microcapsules. The entire suspension then is added to a large volume of the nonsolvent which precipitates any remaining dissolved polymer and hardens the outer membrane of the Dual Microcapsule. The Dual Microcapsules then are recovered, optionally given a surface treatment to modify the permeability characteristics of the outer membrane, and dried.

In the process, the preferred solvents for use are halogenated hydrocarbons having boiling points less than about 65° C. and esters prepared from alkanols containing 1-4 carbon atoms and alkanoic acids containing 1-4 carbon atoms. Particularly suitable solvents are methylene chloride, chloroform and ethyl acetate. Suitable nonsolvents are liquid hydrocarbons such as hexane, heptane, nonane cyclohexane, certain fluorocarbons such as Freon* TF, and the like.

*Registered Trademark of E. I. Dupont.

The Mini-Microcapsules employed in the preparation of the Dual Microcapsules can be prepared by any of the processes known and reported in the art. When the Mini-Microcapsules employed have a PLA membrane, they preferably are prepared by the novel modified processes subsequently described.

The membrane employed as the outer member of the Dual Microcapsule and the membrane of the Mini-Microcapsule can be fabricated from any polymeric material customarily employed for such purposes. Typical polymeric materials which can be employed include cellulose acetate butyrate (CAB), d,l-polylactide (PLA), including its copolymers, cellulose ethers and esters, polyesters, polylactones, polyamides, silicone rubbers, collagen, and the like. The polymeric material employed will be selected to be semipermeable to the Conjugate and/or Functional Agent to be encapsulated and/or formed within the Dual Microcapsules. When the Dual Microcapsules are to be employed for injection into or ingestion by a host, it is desirable to employ in the membranes polymeric materials which are nontoxic to the host, particularly CAB and PLA.

The diffusion rates of materials encapsulated within the Dual Microcapsules are a function both of the encapsulated materials and the polymeric material from which the membranes are fabricated. The diffusion rates can be modified by giving the membranes a physical or chemical treatment subsequent to their preparation. This can be done by suspending the capsules in a nonsolvent medium containing a chemical reactive with the polymeric material included in the membrane. Diisocyanates such as TDI can be employed for this purpose, particularly when the polymeric membrane contains reactive hydrogen atoms.

The inclusion of a Mini-Microcapsule in a dual microcapsule makes possible significantly greater control of the time period over which a drug can be released to a host. Drug-containing microcapsules presently employed in the medical arts have so-called "zero-order solute release rates". That is to say, the drug delivery through the membrane is essentially independent of the amount of drug within the microcapsule. With such microcapsules, the time period over which the drug is released therefrom is controlled nearly exclusively by the solubility of the Drug included within the Microcapsule and the wall permeability to the Drug.

By employment of the Dual Microcapsule of the invention, the effective period over which a Drug can be released to a host can be controlled by either or both of two mechanisms. One mechanism consists of encapsulating the Drug within a Mini-Microcapsule having a membrane with low permeability for the encapsulated drug. The liquid in which the Mini-Microcapsule is suspended and the outer membrane of the Dual Microcapsule will be selected so that the Drug diffusion rate through the outer membrane is significantly greater than the corresponding rate through the membrane of the Mini-Microcapsule. As readily perceived, the effective Drug release rate to the host is controlled by the diffusion rate of the Drug through the Mini-Microcapsule's membrane. In this type of Dual Microcapsule, the medium in which the Mini-Microcapsule is suspended serves principally as a transport medium for the Drug.

A more sophisticated and preferred mechanism involves the use of Conjugate/Deconjugate Agent systems. In this embodiment of the invention, a Drug Conjugate is encapsulated within the Mini-Microcapsule. The Mini-Microcapsule is suspended in a liquid containing a Deconjugating Agent.

As earlier noted, a Drug Conjugate is either a reaction product of a Drug and a Carrier or a complex formed between the Drug and the Carrier. The diffusion rate of the Drug Conjugate through the Mini-Microcapsule's membrane ordinarily will be considerably lower than the diffusion rate of the free Drug through the Mini-Microcapsule's membrane. When the Drug Conjugate enters the liquid containing the Deconjugating Agent, the two materials will interreact with each other to reform or release the Drug. The free drug then diffuses through the outer membrane of the Dual Microcapsule into the host. As can be readily recognized, the overall Drug release rate to the host is controlled by two other rates, specifically, the diffusion rate of the Drug Conjugate through the Mini-Microcapsule's membrane and the rate at which the Drug Conjugate reacts with the Deconjugating Agent.

A Drug Conjugate system well suited for use with the Dual Microcapsules of the invention is a Drug Conjugate formed by reacting a Drug containing a carboxyl group with a mono- or di-glyceride fatty acid ester. A typical Drug-glyceride Conjugate of this type is the ester obtained by reacting aspirin with glyceryl distearate. This Conjugate has a molecular weight 786 as compared with the molecular weight of 180 for aspirin. The preparation of such Conjugates is shown by G. Jones, *Chemistry and Industry*, June 7, 1980, page 452.

The aspirin can be esterified with the diglyceride in the presence of triphenyl phosphine and diethyl azo-dicarboxylate as described by R. Aneja et al., *Journal of Chemical Society, Chemical Communications*, 1974, page 963. The intermediate glyceryl distearate can be prepared by the method described by P. H. Bentley and W. McCrae, *Journal of Organic Chemistry*, 35, 2082 (1970).

A number of enzyme systems will function as Deconjugating Agents for the above-described Drug-glyceride Conjugates. Two effective enzymes are serum esterases and pancreatic lipase. These enzymes cleave the Drug—also the fatty acid—from the glyceride. The freed Drug, the lower molecular weight bound Drug fragments (principally the ester between the Drug and either glycerine or glyceryl monostearate) and possibly minor quantities of the original Drug Conjugate will diffuse across the outer membrane of the Dual Microcapsule to enter the host. The original Conjugate and its fragments containing still-bound Drug will be further cleaved by the enzyme systems in the host to release the Drug.

Another Drug Conjugate system of interest for use in the Dual Microcapsules of the invention are Conjugates formed between Drugs containing a hydroxyl group or an amine group and a polymeric acid such as polyglutamic acid. Several enzyme systems including gamma-glutaminase and carboxypeptidase Y function as effective Deconjugating Agents for such Drug Conjugates.

Polyglutamic acid is commercially available as the sodium salt in a range of molecular weights from about 2,000 to 100,000 daltons. Polyglutamic acid has a pendant carboxyl group for each monomer unit of the polymer. Drugs containing hydroxyl or amine groups can be reacted with the pendant carboxyl groups to form the Drug Conjugate. A broad range of drug loadings can be provided, which allows for the tailoring of the level of Drug loading with the rate of enzymatic deconjugation so as to optimize the Drug release rate.

A Drug Conjugate of this type which can be employed in the Dual Microcapsules of the invention to lower systemic blood pressure is the Conjugate formed between dopamine and a polyglutamic acid having a molecular weight in the range of 2,000 to 15,000. The dopamine is reacted with the polyglutamic acid in an aqueous medium containing 1-ethyl-3-(3'-dimethyl amino propyl)carbodiimide. The reaction conditions are selected so that one molecule of dopamine is reacted for each 10–20 glutamic groups present in the polyglutamic acid.

Another Drug Conjugate system of interest is the Conjugate that can be formed between 17-alphahydroxyprogesterone and polyglutamic acid. The hydroxyprogesterone is reacted with pendant carboxyl groups of the polyglutamic acid. The chemical linkage between the two components, of course, is an ester group. The esterification can be carried out employing mixed-phase reaction systems of the type reported in the literature. The reaction conditions will be selected so that one molecule of the hydroxyprogesterone is reacted for each 10–20 pendant carboxyl groups of the polyglutamic acid.

The enzyme gamma-glutaminase is very efficient at hydrolyzing the gamma-glutaminyl amide of dopamine, but not the aspartyl, succinyl or glutaryl amides of dopamine. The enzyme, carboxypeptidase Y (CPY) is an exopeptidase, and cleaves peptide bonds sequentially to release individual amino acids from the C-terminus of the polypeptide. The broad specificity of CPY permits it to accept as substrates, polypeptides having modified side chains (R-groups) containing the drug moiety. The CPY removes all L-amino acids from most C-terminal sequences. In the event the Drug confers a distinctly basic character upon the Drug-polypeptide Conjugate, carboxypeptidase B may be substituted for CPY.

Yet another Drug Conjugate system of interest is the class of products that can be prepared from:

1. A polymeric alcohol containing a plurality of hydroxyl groups, e.g., dextran or polyvinyl alcohol,
2. Chloroacetic or alpha-chloropropionic acid, and
3. A Drug containing a functional group reactive with a hydroxyl group.

An ester is first formed between the polymeric alcohol and the chloracetic or the alpha-chloropropionic acid. The chloro group of the resulting ester then is converted to a hydroxyl group by routes known in the art. Finally, a Drug having a carboxyl group (or chemical equivalent) is esterified with the resulting pendant hydroxyl group. Drug Conjugates of this type can be prepared from alpha-methyl DOPA of gamma-aminoisobutyric acid (GABA).

Chymotrypsin and serum esterases can be used to cleave these Drug Conjugates. Chymotrypsin will cleave the Drug Conjugate at the ester carbonyl of the Drug quite readily. The serum esterases will cleave at the ester carbonyl of the glycolic acid moiety equally well. Either position of cleavage will lead to low molecular weight products that permeate the outer wall of the Dual Microcapsules.

Other Conjugate systems can be developed which are stable above or below a given pH maintained within the Mini-Microcapsule. Examples of such Conjugates are salts formed from Drugs containing a basic function such as an amino group and a polymeric acid such as polyacrylic acid, an ethylene-maleic anhydride copolymer, an acidic ion-exchange resin and the like. Alternatively, the conjugate can be formed between a Drug containing an acidic function and a high molecular weight base. An aqueous medium buffered to a selected pH can function as a Deconjugating Agent for such Conjugates.

PLA microcapsules are one of the preferred embodiments of the invention. Such PLA microcapsules are difficult to prepare by the Phase Separation Encapsulation Process defined earlier herein. Specifically, when the nonsolvent liquid is added to the PLA-containing solvent solution to encapsulate the core material, it is observed that the PLA-encapsulated product appears to have a tacky exterior coating. The encapsulated spheres tend to agglomerate into oversized clusters that are too large for use.

One of the aspects of the present invention is to provide a reliable process for preparing PLA microcapsules. In the first step of this process, the PLA is dissolved in a miscible mixture of a solvent and a nonsolvent. The solvent and nonsolvent will be employed in a ratio such that the resulting PLA solution prepared therefrom is very close to its phase separation point. As will be readily recognized, the precise ratio of the solvent and nonsolvent employed will depend both upon the specific solvent and nonsolvent employed as well as the concentration of PLA desired in the solution at its phase separation point. A convenient way to prepare the PLA solution is to dissolve the PLA in pure solvent, add sufficient nonsolvent to cause incipient PLA phase separation, and then add the smallest quantity of solvent to redissolve the small quantity of separated PLA.

For reasons which will become apparent from the subsequent descriptions, it is important that the solvent employed have a vapor pressure significantly higher than the vapor pressure of the nonsolvent at the temperature employed to precipitate PLA in the third step of the process subsequently described.

In the second step of the process, the PLA-containing homogeneous solution prepared in the first step of the process is vigorously agitated and the functional core material is added. The agitation provided will be sufficient to disperse these materials uniformly throughout the continuous PLA-containing solvent solution as a fine suspension.

In the third step of the process, agitation is continued to maintain the core material dispersed throughout the PLA-containing solvent solution. Conditions are established to vaporize solvent and nonsolvent from the suspension. While both solvent and nonsolvent will be vaporized and removed from the suspension, the solvent will be removed in greater quantities than the nonsolvent by reason of the solvent's higher vapor pressure. The preferential removal of solvent from the system, of course, changes the ratio of the solvent and nonsolvent liquid in which the PLA is dissolved. Since the PLA-containing solution as prepared is near its saturation point for PLA, as the composition of the solvent/nonsolvent medium is changed, the PLA will undergo a phase separation. The phase separated PLA migrates to the surface of the finely dispersed core droplets or particles and begins encapsulation thereof. After a sufficient quantity of PLA has encapsulated the core droplets or particles, the resulting complex dispersion is ready for transfer to the fourth step of the process.

In the fourth step of the process, the complex suspension from the third step of the process is transferred into an agitated mass of nonsolvent. Upon contacting the nonsolvent to which the suspension is added, any PLA remaining dissolved in the initial solvent solution is precipitated. A second phenomenon which is believed to occur is the extraction of the residual solvent from the PLA membrane.

In carrying out the process, the solvent/nonsolvent mixture employed in the first step of the process should have the requisite solubility to dissolve a convenient quantity of PLA. It is desirable to employ solvent/nonsolvent mixtures which will dissolve at least about 0.3 part by weight of PLA per 100 parts by volume of solvent/nonsolvent mixture at ambient temperature. It also is desirable to employ solvent/nonsolvent mixtures having relatively sharp changes in PLA solubility capacity with temperature. The presently preferred solvents for use in the process are halogenated hydrocarbons having an atmospheric boiling point of less than about 65° C. and esters formed between alkanols containing 1-4 carbon atoms and alkanoic acids containing 1-4 carbon atoms. Suitable halogenated hydrocarbons of this class include methylene chloride and chloroform. The preferred ester is ethyl acetate. The nonsolvents presently preferred for use in the process are hexane, cyclohexane, heptane, selected mineral spirits, nonane, Freon* TF and the like.
*Registered Trademark of E. I. Dupont.

In the third step of the process, after the core materials are uniformly dispersed throughout the polymer solution, conditions are established to vaporize the solvent and nonsolvent from the suspension. This can be done by reducing the pressure on the suspension by drawing a slight vacuum on the system or supplying heat to the suspension, or both. In the embodiment of the invention in which methylene chloride or chloroform is employed as the solvent and an aliphatic hydrocarbon, such as hexane or heptane, is employed as the nonsolvent, vigorous agitation is sufficient to supply the small quantity of energy required to vaporize the requisite quantity of solvent to initiate phase separation of the PLA.

In carrying out the fourth step of the process, care should be exercised to transfer the entire suspension from the third step of the process into the agitated nonsolvent before the encapsulated core materials begin agglomeration into oversized aggregates, presumably by reason of the somewhat tacky nature of the encapsulating PLA membrane at this stage of the process. The approprite point at which the suspension should be transferred to the agitated nonsolvent can be readily established with a minimum of experimentation. It has been the applicant's observation that in preparing batches of the size subsequently described in the working examples, the suspension should be transferred to the agitated nonsolvent in a time period of between 3 and 10 and preferably 4-7 minutes after the initial phase separation of the PLA is observed in the third step of the process.

In the final step of the process, it is desirable to transfer the suspension from the third step of the process into a large excess of the nonsolvent, e.g., 3-20 times the total volume of the solvent solution employed in the first step of the process.

The process described above is carried out under essentially isothermal conditions and preferably at ambient temperatures.

Although not presently preferred, it is possible to heat the PLA solution in the first step of the process to a temperature somewhat above ambient temperature. As the temperature drops in carrying out the second and third steps of the process, the lowering of the temperature accelerates the phase separation of the PLA.

Cellulose acetate butyrate (CAB) is one of the preferred polymeric materials for use in preparing the membrane of the Mini-Microcapsules and the outer membrane of the Dual Microcapsules. Mini-Microcapsules and Dual Microcapsules including such CAB membranes can be prepared by the Phase Separation Encapsulation Process described earlier herein.

It has been noted, however, that minor difficulties are encountered which lengthen the process cycle for preparing either of the above-type capsules from CAB. Specifically, CAB is somewhat difficult to dissolve in the chlorinated hydrocarbon solvents preferred for use in the process. Specifically, when the particulate CAB is added to the solvent, the CAB particles swell, become agglomerated with each other, and take relatively long periods of time to dissolve to form the true solutions required in the capsule formation process. This difficulty can be significantly ameliorated by first suspending the CAB particles in a small volume of the nonsolvent to be subsequently used in the process, preferably a liquid hydrocarbon such as hexane, heptane or octane. When the CAB solvent, e.g., methylene chloride, is added to the suspension with stirring, the CAB particles readily dissolve. Thereafter, the remaining steps of the process are conventional.

The following examples are set forth to illustrate certain principles and practices of the invention to those skilled in the art. The examples have been run to illustrate the fundamental principle of controlling the release rate of a Functional Agent from the dual microcapsules. Details of the action of the ultimately transferred Functional Agent upon the host are not set forth, since such action per se is known.

EXAMPLE 1

This example illustrates the preparation of a dual microcapsule in which a Mini-Microcapsule having India Ink encapsulated in a CAB membrane and a saline solution are encapsulated in a CAB membrane. A charge of 1.6 grams of particulate CAB was made to a 400 ml extraction flask which contained 40 ml of n-hexane. A charge of 130 ml of methylene chloride (dichloromethane, MDC) was added to the dispersion. The system was continuously agitated with a GT21 variable speed laboratory stirrer and stirring rod set at a speed of 2.5 (fast drive gear ratio). The polymer (CAB) dissolved in less than a minute, at which time 15 grams of an aqueous core material were added. The aqueous core was composed of 13 grams of phosphate buffered saline solution plus 2 grams (wet weight) of previously prepared mini-microcapsules, having average diameters of less than 105 μm, and having an India Ink suspension encapsulated therein.

The India Ink containing Mini-Microcapsules were used to allow the formed Dual Microcapsules to be photographed. After the aqueous core droplets were dispersed, 86 ml of n-hexane was added gradually over a thirty minute period (about 3 ml/minute). The action caused phase separation of the CAB and encapsulation of the Mini-Microcapsules and the saline solution. The dispersion was then siphoned into a beaker which contained 800 ml of n-hexane. During this transfer, both the dispersion and the n-hexane were being stirred with the GT21 variable speed stirrer and stirring rod set at a speed setting of 2.5 (fast drive gear ratio). After fifteen minutes of stirring, the product was filtered using a Buchner funnel (about 20 cm diameter), filter paper (#589 Black ribbon) and an aspirator. The filtered product was humid air-dried for about 24 hours. The product was then bottled and stored at room temperature.

EXAMPLE 2

This example illustrates the preparation of a dual microcapsule in which a Mini-Microcapsule having India Ink encapsulated in a CAB membrane and a saline solution are encapsulated in a PLA membrane. Make a charge of 1.1 grams of particulate PLA (code 35614-19) to a 250 ml extraction flask containing 75 ml of methylene chloride (dichloromethane, MDC). Agitate the system using a GT21 variable speed laboratory stirrer and stirring rod set at a stirrer speed of 2.5 (fast drive gear ratio). After the PLA has completely dissolved, add nonane to the solution until a cloud-point develops (i.e., to the point where the polymer begins to precipitate). Approximately 78 ml will be required. Then add MDC dropwise with stirring until the solution is clarified. Add an aqueous core containing ten grams of phosphate-buffered saline solution plus 1 gm (wet weight) of previously prepared Mini-Microcapsules containing the India Ink suspension. Continue vigorous stirring until PLA first precipitates by reason of MDC evaporation. Stir for an additional 6 minutes and siphon the resulting slurry into a beaker containing 3,500 ml of n-heptane and surfactant. Stir the n-heptane and the surfactant during transfer using similar stirring equipment and a stirrer speed of 2.5 (fast drive gear ratio). Stir for an additional 5 minutes, then recover and dry the Dual Micocapsules as described in Example 1.

To demonstrate the effectiveness of the Dual Microcapsules of the invention, employing Conjugate/Deconjugating Agents therein, in controlling the diffusion rate of a Functional Agent from the microcapsules, experiments were run employing glucose (MW=180 daltons) or glucose precursors as the Functional Agent.

Four lots of Dual Microcapsules were prepared. In all experiments, CAB was used in both the Mini-Microcapsule membranes and the outer membranes. In lot "A" a 10% glucose solution was included in the Mini-Microcapsules with the suspending liquid being a phosphate buffered saline solution (pH=7.3). Lot "B" differed from lot "A" in that a 10% dispersion of potato starch sold under the trade designation DIFCO was included in the Mini-Microcapsules. Lot "C" differed from lot "B" in that a small quantity of alpha-amylase was included within the Mini-Microcapsules to slowly convert the starch to reducing sugars. Lot "D" differed from lot "C" in that a small quantity of gluco-amylase was included in the suspending saline solution. This enzyme will convert reducing sugars to glucose.

The construction of the dual microcapsules are summarized in Table I together with the product(s) expected to be obtained by diffusion of their contents through the outer membrane into an aqueous medium.

TABLE I

| Capsule System | Interior Capsule Contents | Exterior Capsule Contents | Expected Results |
|---|---|---|---|
| "A" | 10% glucose | buffer only | rapid glucose release |
| "B" | 10% potato starch | buffer only | no glucose release; no reducing sugars release |
| "C" | 10% potato starch & alpha-amylase | buffer only | no glucose release; slow reducing sugars release |
| "D" | 10% potato starch & alpha-amylase | gluco amylase | prolonged glucose release; maybe slow reducing sugars release |

The Dual Microcapsules were evaluated in in vitro experiments. Two grams of capsules were placed in five milliliters of aqueous test solution (pH 5.5 buffer). The solutions were filtered and assayed for the presence of glucose and reducing sugars. Fresh test solution was added back to the capsules at each predetermined time point. In this experiment, the reducing sugar test quantifies glucose plus higher polysaccharides combined, but the glucose meter used is specific for glucose only. The results of the experiment are shown in Table 2.

TABLE 2

| | CUMULATIVE RELEASE (mg glucose or mg reducing sugar expressed as glucose) | | | | | |
|---|---|---|---|---|---|---|
| | ½ hour | | 4 hours | | 20 hours | |
| capsule system | glucose | non-glucose reducing sugars | glucose | non-glucose reducing sugars | glucose | non-glucose reducing sugars |
| "A" | 10 | 0 | 13 | 0 | 14.6 | 0 |
| "B" | 0 | 0 | 0 | 0 | 0 | 0 |
| "C" | 0 | 1.9 | 0 | 4.4 | 0 | 7.3 |
| "D" | 0.6 | 0.5 | 1.0 | 0.5 | 1.0 | 0.5 |

The results show that:

1. Glucose was rapidly released from the "A" capsules as expected.
2. No carbohydrate was released from the "B" capsules either as glucose or higher polysaccharides, as expected.
3. The addition of alpha-amylase in the "C" capsules caused the slow release of the higher polysaccharides without producing glucose.
4. With the "D" capsules, glucose was released, but not over the entire 20-hour period.

The experiment demonstrates the operating principle of the Dual Microcapsules. The failure to release glucose from the "D" capsules over the entire 20-hour period doubtlessly resulted from inadequate glucoamylase activity for the continued hydrolysis of the higher polysaccharides. This shortcoming can be corrected by modifying enzyme activity within the exterior capsule of the "D" capsules.

As earlier noted, the preferred embodiments of the invention have a Conjugate (usually dispersed in an aqueous medium) encapsulated within the mini-microcapsules and have the Deconjugating Agent dispersed in an aqueous medium in the space intermediate of the mini-microcapsule membrane and the outer membrane. The Conjugate will diffuse through the mini-microcapsule membrane whenever the dual microcapsules contain water. As earlier noted, to prolong the effective shelf-life of the dual capsules, shortly after their preparation they should be dehydrated to form the Crenate Shape earlier discussed and illustrated in FIG. 1A. The dehydration step can be carried out by mild heating, drying in a vacuum oven, or in some cases, simply upon standing in air where the membranes are very permeable to water. The Dual Microcapsules, after being dehydrated, should be stored in sealed containers and preferably under anhydrous conditions. Shortly before use, the dehydrated Dual Microcapsules will be rehydrated by being steeped in water.

Alternate means can be employed to extend the shelf-life of the Dual Microcapsules. One such technique is to encapsulate the Functional Agent within a Mini-Microcapsule whose membrane is essentially totally impermeable to the Functional Agent. The Mini-Microcapsule membrane in this embodiment will be prepared from a polymeric material different from the polymeric material employed to prepare the outer membrane of the Dual Microcapsule. The polymer included in the membrane of the Mini-Microcapsule will be fabricated from a material which can be ruptured or degraded by a treatment process having no corresponding effect upon the outer membrane of the Dual Microcapsule. Treatments of the type visualized are microwave radiation, ultraviolet radiation, laser radiation, treatment with ultrasonic vibrations and the like. Alternatively, the membrane of the Mini-Microcapsules can be fabricated from a friable polymer while the outer membrane is fabricated from a flexible polymer. The Mini Microcapsules' walls can be ruptured by application of a compressive force. In this embodiment of the invention, of course, the rate of release of the Functional Rate to the host will be controlled solely by its diffusion rate through the outer membrane of the Dual Microcapsule.

The Dual Microcapsules of the invention can be employed to deliver various types of medication to mammals, including both man and domestic animals. Materials which can be administered effectively include contraceptive materials, narcotic antagonists, cardiac arrhythmia agents, chemotherapeutic drugs and various veterinary products.

The Dual Microcapsules of the invention also can be employed to provide a prolonged release of Functional Agents other than drugs. Among the Functional Agents of the type that can be delivered include herbicides, fertilizers, growth regulator substances, deodorizers, pheromones and other like materials.

While the processes and products herein described constitute preferred embodiments of the invention, it is to be understood that the invention is not limited to these precise processes and products, and that changes may be made therein without departing from the scope of the invention which is defined in the appended claims.

What is claimed is:

1. Dual Microcapsules having encapsulated therein at least two liquids and comprising:
   (a) an outer polymeric membrane encapsulating a first liquid, and
   (b) at least one Mini-Microcapsule suspended in said first liquid, said Mini-Microcapsule(s) having polymeric membrane(s) encapsulating a second liquid;
   said Dual Microcapsules being further characterized in that;
   (c) the second liquid contains therein a Conjugate formed between a Functional Agent and a Carrier,
   (d) the first liquid contains therein a Deconjugating Agent,
   (e) the polymeric membrane(s) of the mini-microcapsule(s) are at least semipermeable with respect to the Conjugate so that said Conjugate can diffuse therethrough and into said first liquid at a controlled preselected rate,
   (f) the Conjugate and the Deconjugating Agent are interactive with each other to release or reform the Functional Agent from the Conjugate, and
   (g) the outer polymeric membrane is at least semipermeable with respect to the Functional Agent so that said Functional Agent can diffuse therethrough at a controlled preselected rate.

2. Dual Microcapsules of claim 1 in which the Conjugate is formed between a low molecular weight Functional Agent and a Carrier.

3. Dual Microcapsules of claim 2 in which the low molecular weight Functional Agent has a molecular weight of less than about 1,000.

4. Dual Microcapsules of claim 2 in which the Deconjugating Agent is a deconjugating enzyme.

5. Dual Microcapsules of claim 4 in which the Conjugate is a Drug Conjugate.

6. Dual Microcapsules of claim 1 in which the mini-microcapsules have diameters in the range of about 1 μm to about 1 mm.

7. Dual Microcapsules of claim 6 which have diameters in the range of about 10 μm to about 2 mm.

8. Dual Microcapsules having encapsulated therein at least two materials and comprising an outer polymeric membrane encapsulating:
  (a) at least one Mini-Microcapsule having encapsulated therein a substantially dry, but readily hydrateable Conjugate formed between a Functional Agent and a Carrier, and
  (b) a substantially dry but readily hydrateable Deconjugating Agent between the membrane of the Mini-Microcapsule and the outer membrane;
said Dual microcapsule being further characterized in that;
  (c) the entire microcapsule, including the mini-microcapsule(s) encapsulated therein, has a Crenate Structure,
  (d) the outer membrane and the membrane(s) of the mini-microcapsules are at least semipermeable to water, and
  (e) the dual microcapsule will, when contacted with water, imbibe water so as to disperse both the Conjugate and the Deconjugating Agent in aqueous media which are kept out of direct contact with each other by the membrane(s) of the mini-microcapsule(s);
said dual microcapsule being further characterized in that;
  (f) The membrane(s) of the Mini-Microcapsule(s) are at least semipermeable with respect to the Conjugate so that said Conjugate can diffuse therethrough and into the aqueous medium containing the Deconjugating Agent at a controlled preselected rate; and
  (g) The outer membrane is at least semipermeable with respect to the Functional Agent so that said Functional Agent can diffuse therethrough at a controlled preselected rate.

9. A Dual Microcapsule of claim 8 in which the Conjugate is formed between a Functional Agent and a Carrier.

10. A Dual Microcapsule of claim 9 in which the Conjugate is a Drug Conjugate and the Deconjugating Agent is a deconjugating enzyme.

11. Dual Microcapsules having encapsulated therein at least two materials and comprising:
  (a) an outer polymeric membrane encapsulating a liquid which contains therein a Deconjugating Agent, and
  (b) at least one Mini-Microcapsule suspended in said liquid, said Mini-Microcapsule having a polymeric membrane encapsulating a Conjugate formed between a Functional Agent and a Carrier;
said Dual microcapsule being further characterized in that;
  (c) the polymer included in the membrane(s) of the Mini-Microcapsule(s) is different from the polymer included in the outer polymeric membrane and is decomposable by a treatment which will not decompose the outer membrane;
said dual microcapsule being further characterized in that;
  (d) The outer membrane is at least semipermeable with respect to the Functional Agent so that said Functional Agent can diffuse therethrough at a controlled preselected rate.

12. Dual Microcapsules of claim 11 in which the membrane(s) of the Mini-Microcapsules are decomposable by exposure to laser, microwave or ultraviolet radiation.

13. Dual Microcapsules of claim 11 in which the membranes of the Mini-Microcapsules are friable and the outer membranes are flexible so that a compressive force will rupture the Mini-Microcapsules' membranes without rupturing the outer membranes.

14. Dual Microcapsules of claim 11 in which the membrane(s) of the Mini-Microcapsules are decomposable by exposure to ultrasonic vibrations.

15. A process for preparing Dual Microcapsules having encapsulated therein both a Conjugate formed between a Functional Agent and a Carrier and a Deconjugating Agent which comprises:
  (a) agitating a solution of a polymer in an organic solvent therefor and adding thereto a mixture of;
    (1) an aqueous liquid which is immiscible with said polymer solution and includes therein a Deconjugating Agent, and
    (2) Mini-Microcapsules having a Conjugate encapsulated therein, so as to uniformly disperse said aqueous liquid and said Mini-Microcapsules throughout said polymer solution, and
  (b) agitating the suspension of step (a) and adding thereto an organic liquid which is miscible with the polymer solvent and has little or no solvent power for said polymer in an amount sufficient to cause phase separation of the polymer and encapsulation of the aqueous liquid and the Mini-Microcapsule(s).

16. The process of claim 15 in which the polymer solvent employed is a halogenated hydrocabon or an ester formed between an alkanol containing 1–4 carbon atoms and an alkanoic acid containing 1–4 carbon atoms.

17. The process of claim 16 in which the solvent is methylene chloride, chloroform or ethyl acetate.

18. The process of claim 16 in which the organic liquid employed in step (b) is a liquid hydrocarbon.

19. The process of claim 17 in which the organic liquid employed in step (b) is a liquid hydrocarbon.

20. The process of claim 15 in which the product of step (b) is added to an agitated mass of an organic liquid having little or no solvent power for the polymer to precipitate any remaining dissolved polymer and harden the polymer which has encapsulated the aqueous liquid and the Mini-Microcapsule(s).

21. The process of claim 20 in which the polymer solvent employed is a halogenated hydrocarbon or an ester formed between an alkanol containing 1–4 carbon atoms and an alkanoic acid containing 1–4 carbon atoms and the organic liquid having little or no solvent power for the polymer is a liquid hydrocarbon.

22. The process of claim 21 in which the solvent is methylene chloride, chloroform or ethyl acetate.

* * * * *